United States Patent [19]
Coles et al.

[11] Patent Number: 5,868,725
[45] Date of Patent: Feb. 9, 1999

[54] ABSORBENT ARTICLE HAVING A CUSHIONING MEMBER AND A BARRIER

[75] Inventors: Peter Coles, Kelkheim-Fischbach; Rainer Walter Max Schone, Koenigstein/T's; Michael Divo, Friedrichsdorf; Helene Karin Costea, Worms, all of Germany

[73] Assignee: The Procter & Gamble Company, Cincinnati, Ohio

[21] Appl. No.: 776,098

[22] PCT Filed: Jul. 7, 1995

[86] PCT No.: PCT/US95/08538

§ 371 Date: Jan. 10, 1997

§ 102(e) Date: Jan. 10, 1997

[87] PCT Pub. No.: WO96/01609

PCT Pub. Date: Jan. 25, 1996

[30] Foreign Application Priority Data

Jul. 12, 1994 [EP] European Pat. Off. .............. 94110799

[51] Int. Cl.⁶ ..................................................... A61F 13/15
[52] U.S. Cl. ..................... 604/385.1; 604/378; 604/369
[58] Field of Search .................................. 604/368, 369, 604/378, 385.1, 385.2, 389, 391

[56] References Cited

U.S. PATENT DOCUMENTS

| | | | |
|---|---|---|---|
| H1674 | 8/1997 | Ames et al. | 604/389 |
| 4,778,459 | 10/1988 | Fuisz | 604/378 |
| 4,895,568 | 1/1990 | Enloe | 604/385.2 |
| 4,938,755 | 7/1990 | Forman | 604/385.2 |
| 5,151,091 | 9/1992 | Glaug et al. | 604/385.1 |
| 5,295,986 | 3/1994 | Zehner et al. | 604/385.1 |
| 5,520,674 | 5/1996 | Lavon et al. | 604/369 |

FOREIGN PATENT DOCUMENTS 0 443 082 A1 8/1991 European Pat. Off. .
1 575 363 9/1980 United Kingdom .

*Primary Examiner*—Robert A. Clarke
*Attorney, Agent, or Firm*—Kevin D. Hogg; Steven W. Miller; Jacobus C. Rasser

[57] ABSTRACT

An absorbent article especially adapted for users ranging from walking infants to adults in a pre-dominantly lying-down position, comprises cushioning means in at least the back waist region of the article. A liquid barrier is located between the cushioning means and the absorbent core to prevent liquids from migrating into the cushioning means. In one embodiment, the average basis capacity of the absorbent core is highest in the back half section of the core.

21 Claims, 10 Drawing Sheets

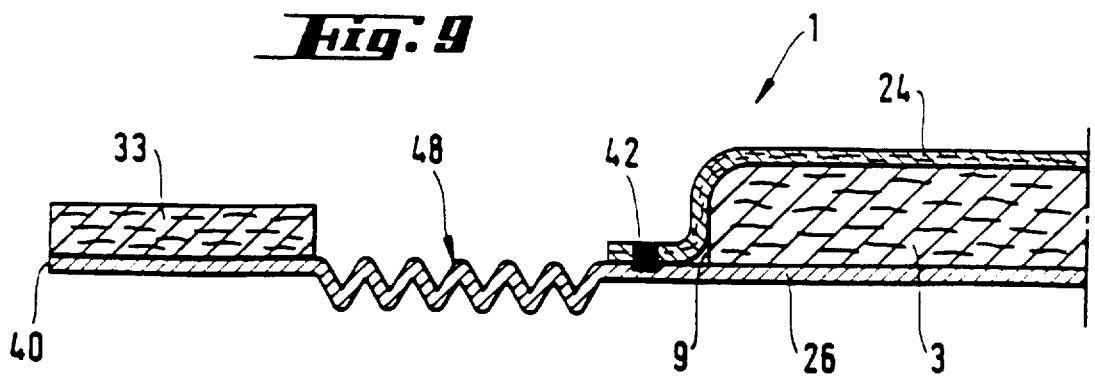
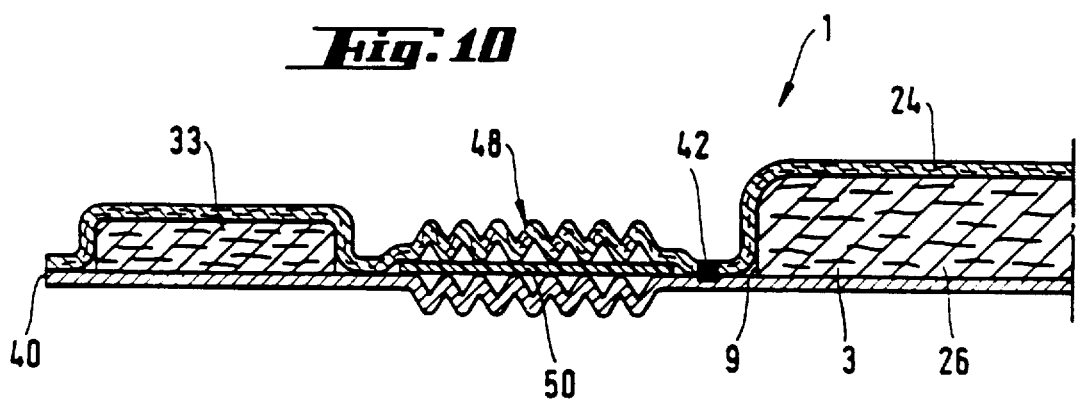
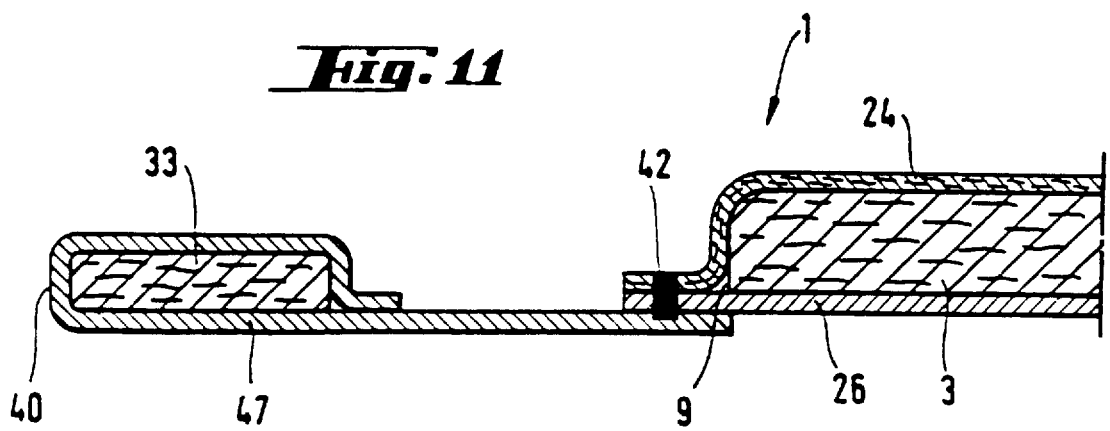

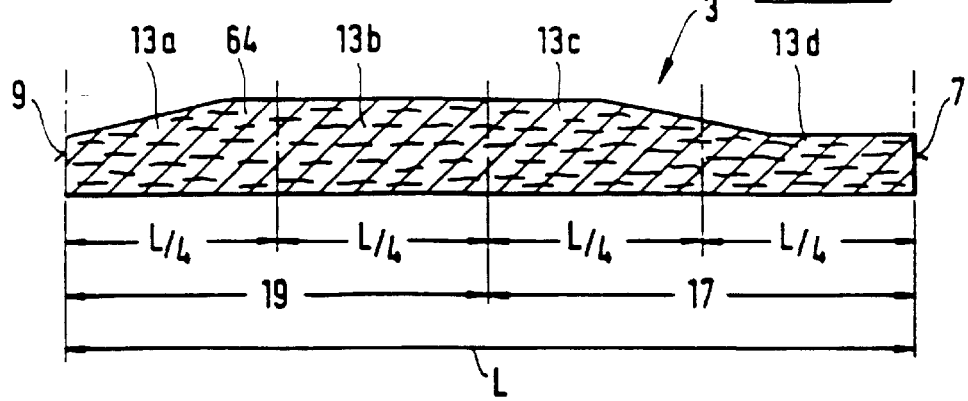
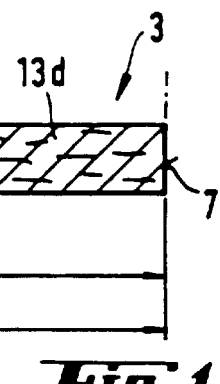
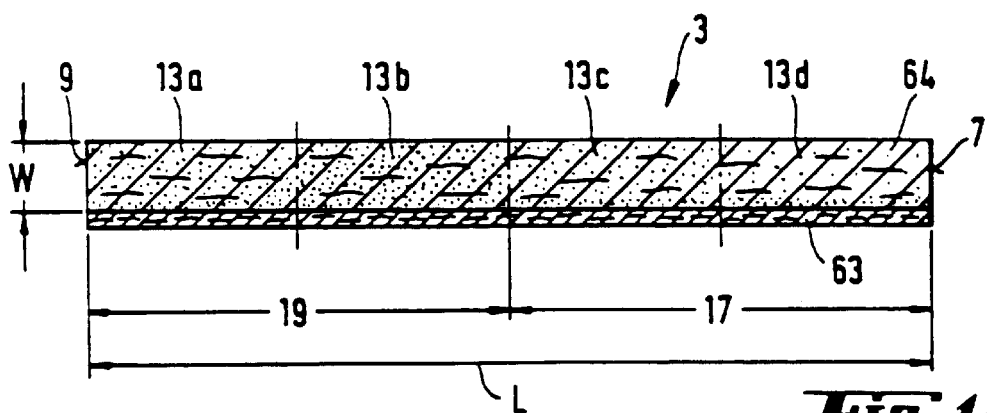
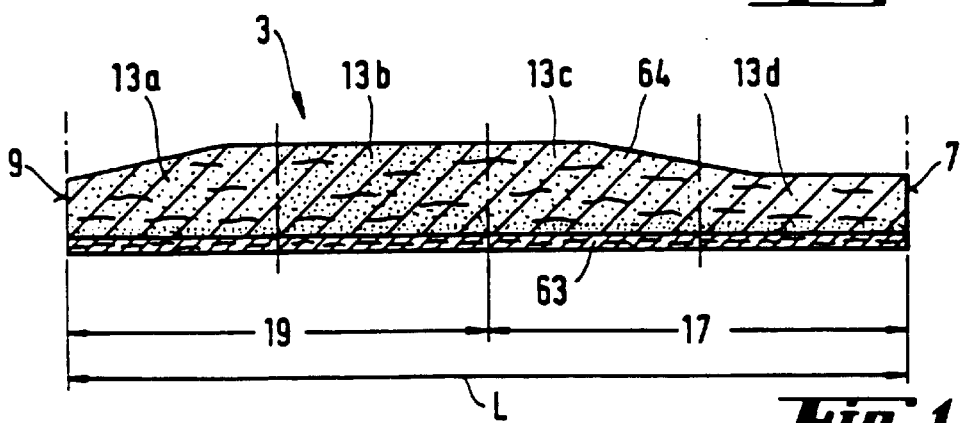

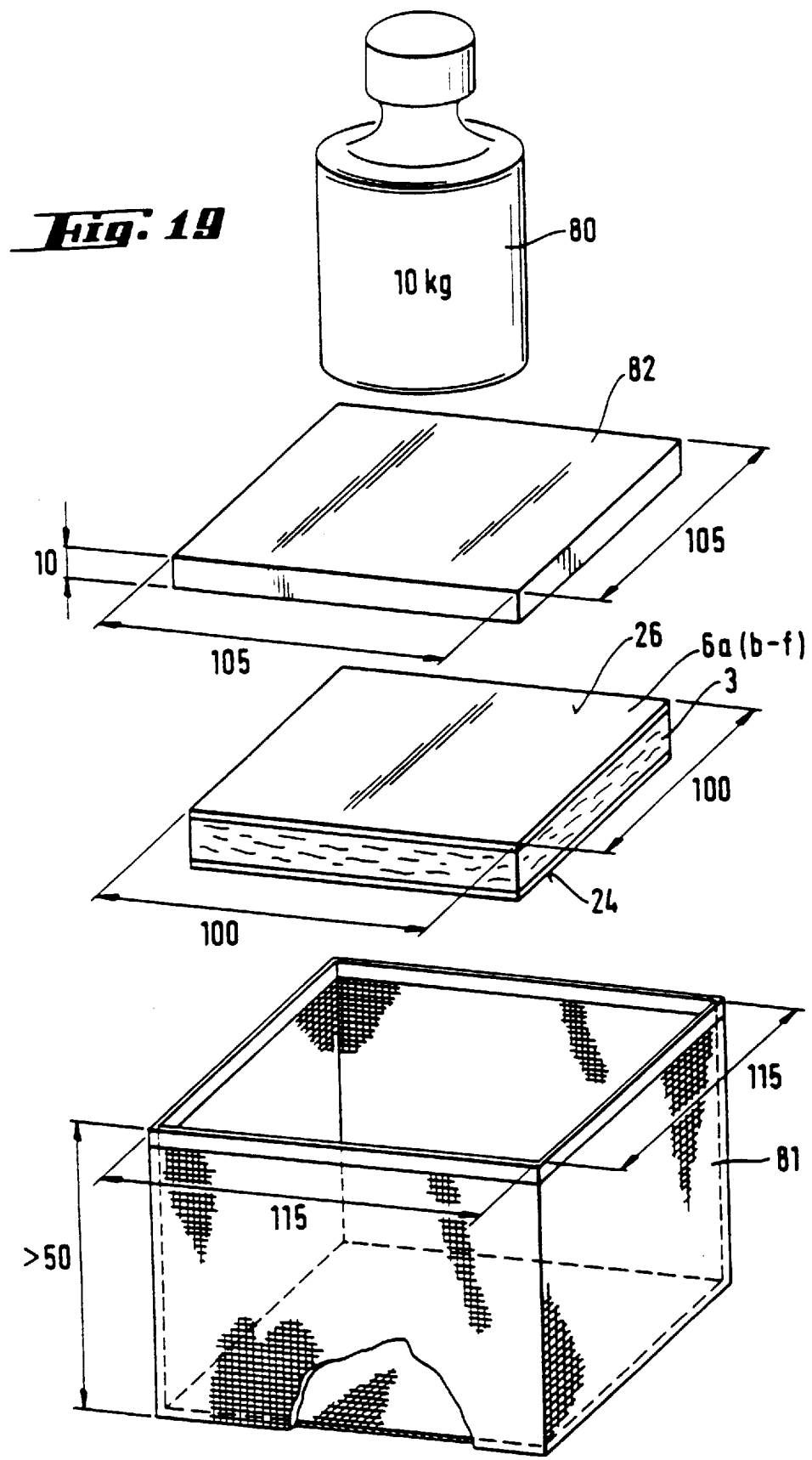

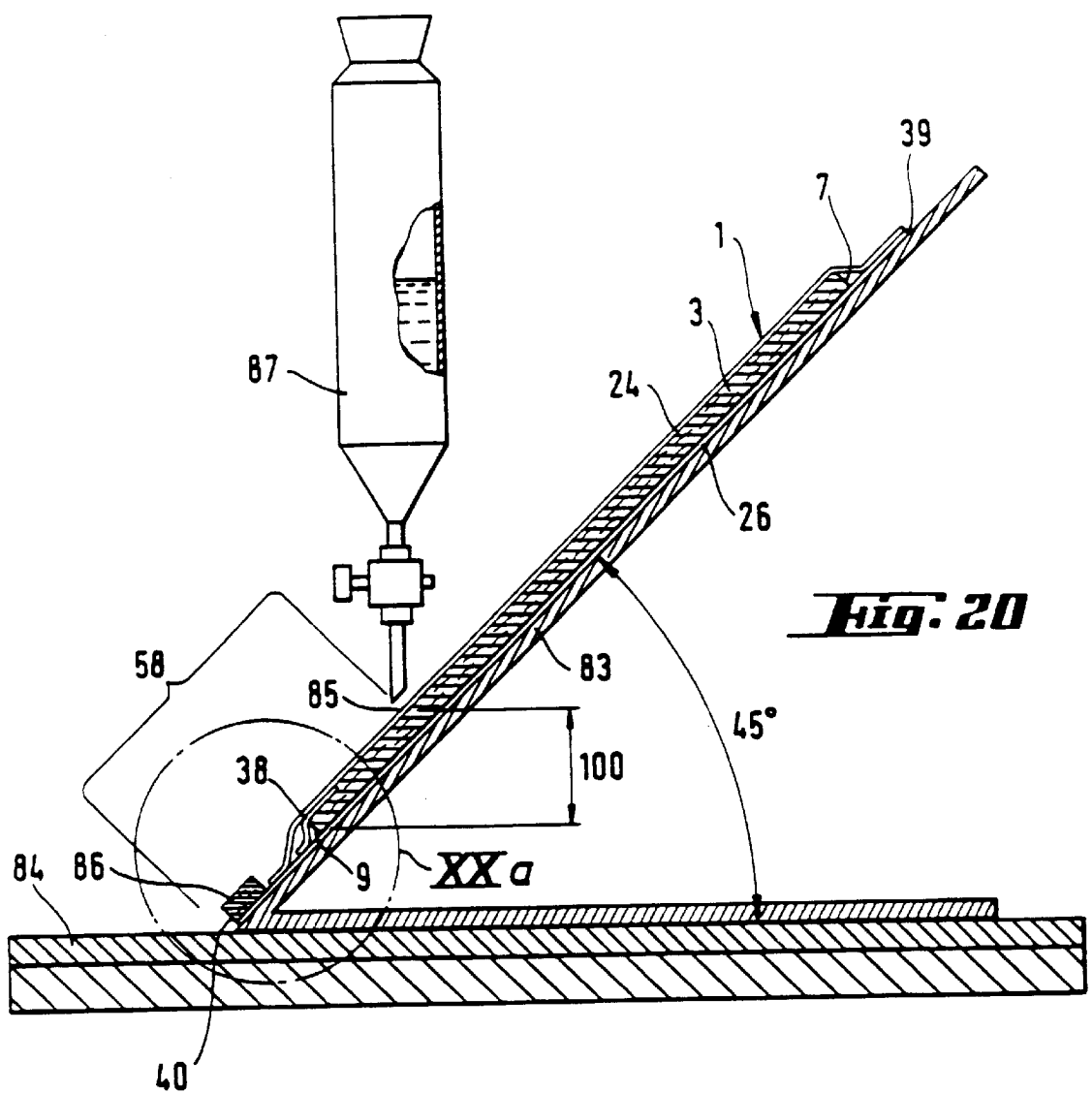
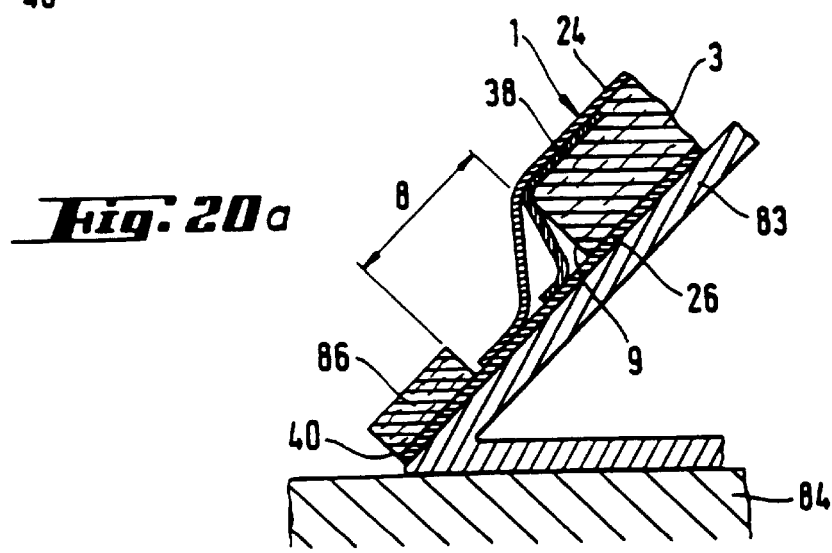

ABSORBENT ARTICLE HAVING A CUSHIONING MEMBER AND A BARRIER

FIELD OF THE INVENTION

The present invention relates to an absorbent article comprising a liquid-permeable topsheet, a liquid-impermeable backsheet and an absorbent core interposed between the topsheet and the backsheet, the backsheet comprising:

a perimeter having a front waist edge (39) and a back waist edge (40), a front waist region adjacent the front waist edge and a back waist region adjacent the back waist edge, the core comprising:

a perimeter having a back transverse edge, a front transverse edge and two longitudinal sides, a back half section located adjacent the back transverse edge and a front half section located adjacent the front transverse edge.

BACKGROUND OF THE INVENTION

In the absorbent product technology, many attempts have been made to optimise the absorbent capacity and efficiency of absorbent cores by providing regions of increased or diminished basis weight and density in such cores. Also, it has been attempted to reduce leakage by providing barrier structures to the absorbent products to reduce liquid migration towards and beyond the perimeter of the absorbent product.

From EP-A-052 413 it is known that for absorbent products, leakage of liquids along the waist edge can be prevented by providing a barrier sheet located between the topsheet and the backsheet and the waist ends of an absorbent article. The barrier sheet overlies the core at a waist end and prevent liquids from being squeezed out of the transverse edges of the core.

From EP-A-376 022 (Robertson) a unitary waistcap-waistband is known, wherein a unitary piece of elastomeric material extends from the perimeter of the absorbent product towards the core. The single piece of elastomeric material provides a waist elastic as well as a stand-up barrier overlying the topsheet at the waist end of the core.

From U.S. Pat. No. 4,695,278 (Lawson) an absorbent article is known comprising an elasticated stand-up barrier cuff in the leg areas.

From U.S. Pat. No. 4,795,454 (Dragoo) an absorbent article is known comprising an elasticated stand-up barrier cuff that is connected with a proximal edge to the absorbent article, and is located adjacent a gasketing cuff. A liquid-pervious topsheet terminates inboard of the proximal edge of the barrier cuff. Seal means are located along the proximal edge to prevent wicking of liquids underneath the barrier cuff.

From EP-B-0 304 631 it is known to coat and seal lateral portions of a liquid-permeable topsheet with a hot-melt adhesive to prevent lateral leakage of liquids.

In U.S. Pat. No. 4,935,022 (Lash) an absorbent structure is disclosed which has a lower storage layer and an upper acquisition/distribution layer comprising chemically stiffened cellulose fibers and absorbent gelling material. The upper acquisition/distribution layer is of larger surface area than the underlying storage layer. The lower storage layer is formed of an insert, which is placed relative to the upper acquisition/distribution layer such that about 75% of the absorbent gelling material in the lower layer is found in the front two-thirds section of the absorbent structure, and at least 55% of the total amount of absorbent gelling material is found in the front half section.

In U.S. Pat. No. 4,685,915 (Hasse) an absorbent product is disclosed having a core comprising hydrophilic fibers and absorbent gelling material, the core having an area of higher average density and basis weight than the end portions of the core. The area of higher average density and basis weight is located near the center or the front of the absorbent product.

In U.S. Pat. No. 4,834,735 (Alemany) an absorbent core is disclosed having a storage zone and an acquisition region of lower average density and basis weight than the storage zone. The core comprises a mixture of hydrophilic fibers and absorbent gelling particles. The acquisition region is located towards the front of the absorbent core.

In European patent no EP-B-0 330 675, it is disclosed to introduce absorbent gelling material into specific locations of a horizontal, or x-y plane of an absorbent core using pulsed powder spray guns.

In International patent application no's WO 91/11163 and WO 91/11165, a dual layer core is disclosed comprising a lower storage layer and an upper fluid acquisition/distribution layer comprising chemically stiffened cellulose fibers, the upper layer being substantially free of absorbent gelling material. The area of the acquisition/distribution layer is between 25% and 100% of the area of the lower storage layer, and is preferably of elongated shape. For adult incontinence products, the acquisition/distribution layer is generally located in the front two thirds of the absorbent article, relative to the backsheet.

In U.S. Pat. No. 4,411,660 (Dawn), an absorbent article is disclosed in which a layer consisting of absorbent gelling material underlies a fibrous layer. The layer of absorbent gelling material can be in the form of particles, fibers or a film.

In International patent application WO 91/04724, a diaper core is disclosed which linearly tapers from a relatively narrow crotch section to a relatively wide back section.

EP-A-0 532 035 discloses an absorbent article especially adapted for newborn babies, having cushion barriers to prevent leakage and reduce redmarking of the very sensitive skin.

It has been found by the applicant that in absorbent products which are intended for use by walking infants or adults in a primarily lying-down position, the combination of a wet structure and a relatively high pressure on certain parts of the anatomy, contributes to development of skin complaints. The majority of adults suffering from a severe incontinence are elderly women, for which leakage in this position is relatively frequent compared to other users.

It is an object of the present invention to provide an absorbent product which provides reduced leakage when used in a lying down position.

It is another object of the invention to provide an absorbent article that is especially adapted for users ranging from walking infants to adults, when confined to a predominantly lying down position.

It is a further object of the invention to provide such an absorbent article which especially reduces leakage among woman users when confined to a predominantly lying down position.

It is still another object of the invention to provide an absorbent structure especially adapted for users ranging from walking infants to adults, which product maintains improved dryness in the lying-down position of the user and in which the negative effects of pressure build-up on specific parts of the anatomy are reduced.

SUMMARY OF THE INVENTION

An absorbent article in accordance with the invention is characterised in that the article comprises in at least the back waist region a cushioning member located between the perimeter of the backsheet and the perimeter of the core for distribution of pressure on a user in the lying down position and a liquid barrier for preventing liquid transport, for instance from the core into the cushioning member. The length of the core along the longitudinal center line is at least 30 cm.

The cushioning member in the back waist region of the absorbent article has as a primary function the distribution of the forces on the back and hips of users which range from walking infants to adults, suffering from incontinence and being confined to a predominantly lying-down position. By maintaining the cushioning member in a dry state during use of the absorbent article, the resiliency of the cushioning member is unaffected and the formation of detrimental skin conditions can be reduced.

The cushioning member need not be absorbent and can for instance be formed from a liquid-impermeable foam material. In this case, the liquid-impermeable outer surface of the cushioning member forms the barrier to prevent liquid from penetrating into the cushioning member.

Preferably, the cushioning member is formed by airfelt and underlies the topsheet. Such a cushioning member is isolated from the core by a sealing line along which the backsheet is connected to the topsheet in a liquid-tight manner. In this case, the absorbent properties of the cushioning member can be advantageously used upon removal of the used article. Upon removal, residual liquid remaining on the skin of the wearer can be wiped off and absorbed by the dry, absorbent cushioning member.

For the cushioning member to properly distribute the pressure on the user, the surface of the cushioning member is preferably larger than 25 cm$^2$ when the cushioning member is located in the side panel areas of the absorbent articles. The side panel areas contact the hips of the wearer in use. For the cushioning member located the hips of the wearer in use. For the cushioning member located along the back waist edge of the core, the surface area is at least 50 cm$^2$.

In an alternative embodiment of an asorbent article in accordance with the invention, the cushioning-member is located adjacent the backsheet. The cushioning member may be placed on the garment-facing side of the backsheet and can in that case be of liquid-permeable material. The backsheet forms a liquid barrier that prevents liquid from entering into the cushioning member.

The cushioning member may comprise a number of air-filled pockets between two thermoplastic sheets, similar to those that are used in the packaging industry. Such "bubble pad" sheets can be located on the garment-facing side or on the user-facing side of the backsheet and can cover the backsheet wholly or partially.

Preferably the area of the backsheet extending between the back transverse edge of the core and the cushioning member is extensible, such that the cushioning member can move independently of the core. In this manner the cushioning member can remain relatively stationary with respect to the wearer in use, as the cushioning members are little affected by movements of the core. In this manner it is prevented that frictional forces are exerted by the cushioning members on the skin of the user.

Preferably the backsheet is elastically extensible at least in the area between the back transverse edge of the core and the cushioning member to closely conform to the body of the wearer. The backsheet may be made elongatable in the above mentioned area, for instance by ringrolling as described in U.S. Pat. No's 5,156,793 (Buell) and 5,143,679 (Weber).

The backsheet in the back waist region may be elasticated by attaching an elastic member to the backsheet in a pre-stretched state, or by gathering the backsheet in that area and attaching an elastic member to the backsheet in its relaxed state. Alternatively, the backsheet and the elastic member can be first mutually connected and can subsequently be passed between two corrugated rolls such that the backsheet becomes extensible.

The backsheet may in the back waist region and/or front waist region be formed by a breathable nonwoven material, preferably by an elastic non-woven material. The backsheet may comprise in its central region a polyethylene film to which the nonwoven material is attached in waist regions.

Preferably, the average basis capacity of the core is largest in the back half section of the core. The average basis capacity is a measure of the amount of liquid that can be absorbed per gram of absorbent material. The average basis capacity will depend on the amount and on the type of absorbent material in the front half section and the back half section. The absorbent material in any one section may comprise for instance absorbent gelling material, fibers, foam, interpartically crosslinked aggregates or any combination thereof. The average basis capacity is measured according to a test method which is based on the official method established by the German "Medizinischer Dienst der Spitzenverbände der Krankenkassen e.V." for reimbursement of incontinence absorbent products. The test method "Prüfmethode Nr. 1/93 MDS-HI Teil 1, Bestimmung der Flüssigkeitsaufnahme " is described in the detailed description of the invention, below. In a preferred embodiment the weight of the absorbent gelling material is larger in the back half section than in the front half section of the core.

Due to the relatively high average basis capacity in the back half section of the core, the liquids which migrate to the back half section of the core under the influence of gravity are effectively confined. Hence improved dryness of the user in the lying-down position results.

In addition to a concentration of the absorbent capacity in the back half section of the core, the absorbent article preferably comprises further barrier means along the transverse waist edge of the core. These barrier means may comprise a z-folded portion of the backsheet or a stand-up elasticised barrier cuff. These barrier means are especially effective in reducing migration of liquids or viscous waste, along the topsheet towards the waist regions, and protect the cushioning members from becoming soiled.

In another embodiment of an absorbent article according to the invention, the backsheet comprises a user-facing side and a garment-facing-side, the cushioning member being located in the back waist region, the article comprising at least two mechanical fasteners comprising a plurality of hook-like fastening projections, the fasteners being connected to the garment facing side of the backsheet in the front waist region for engaging the cushioning member upon use of the article.

The cushioning member provides a landing surface that is elevated above the plane of the backsheet and to which the hook-fastening member can be firmly attached.

BRIEF DESCRIPTION OF THE DRAWINGS

The invention will be explained in detail with reference to the accompanying drawings. In the drawings:

FIG. 9 shows a cross-sectional view of one embodiment wherein the distance between the core and the cushioning members can vary, FIG. 10 shows a cross-sectional view of another embodiment wherein the distance between the core and the cushioning members can vary, FIG. 11 shows a cross-sectional view of another embodiment wherein the distance between the core and the cushioning members can vary, FIG. 12 shows a cross-sectional view of the core of the absorbent article along the longitudinal center line, the core comprising a back half section in which a majority of the absorbent material is located, FIG. 13 shows a cross-sectional view of the core of another embodiment of the absorbent article along the longitudinal center line, the core comprising a back half section in which the majority of the absorbent material is located, FIG. 14 shows a cross-sectional view of the core of another embodiment of the absorbent article along the longitudinal center line, the core comprising a back half section in which the majority of the absorbent material is located, FIG. 15 shows a cross-sectional view of the core of another embodiment of the absorbent article along the longitudinal center line, the core comprising a back half section in which the majority of the absorbent material is located.

DETAILED DESCRIPTION OF THE INVENTION

Figure 1:
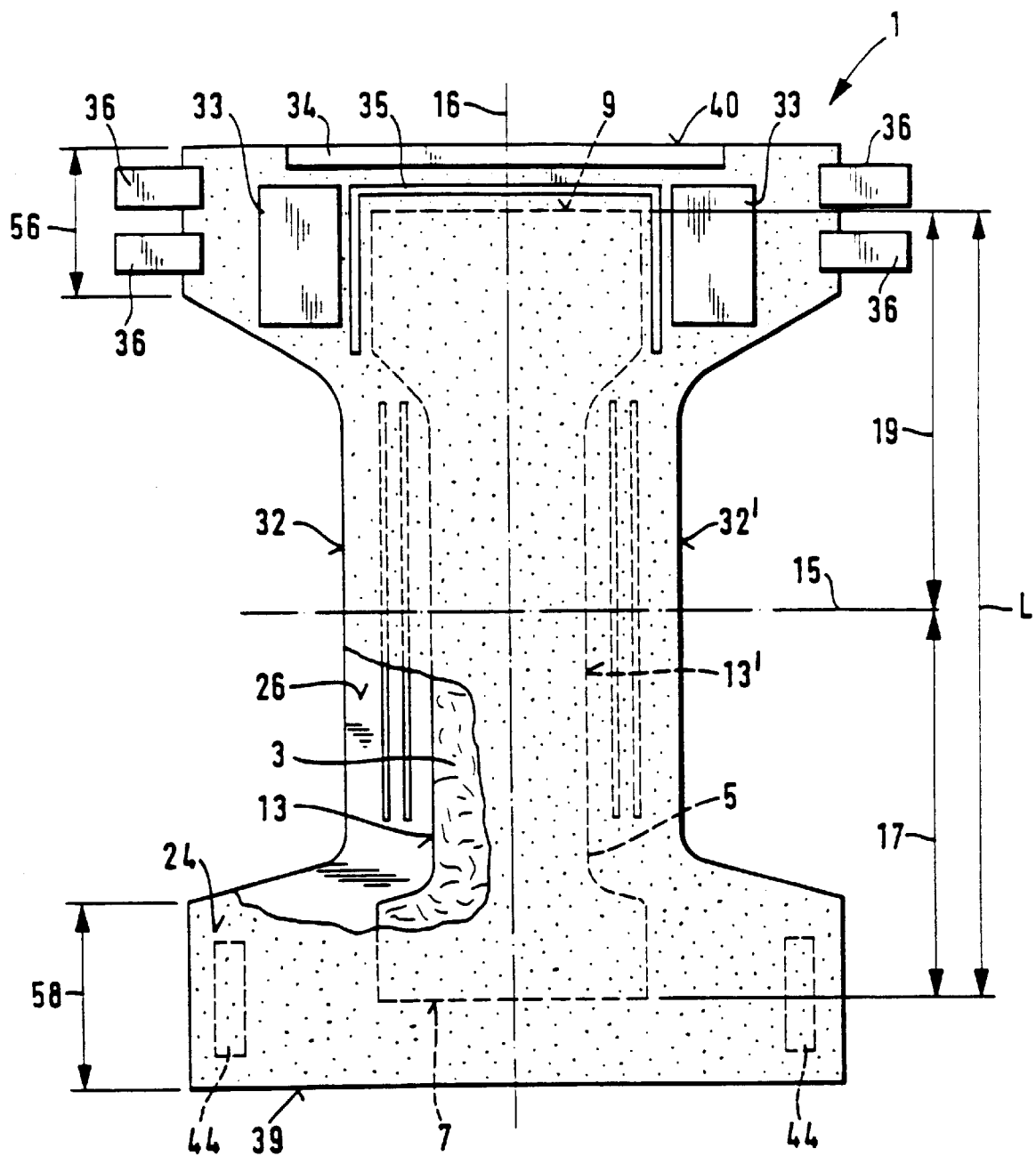
FIG. 1 shows a front elevational view of an absorbent article comprising a cushioning member according to the invention.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, or diaper as shown in FIG. 1. As used herein, the term "diaper" refers to an absorbent article generally worn by walking infants and incontinent persons that is worn about the lower torso of the wearer. In particular, the invention is related to an incontinence product, especially for adults, which product can absorb between 100 and 1000 ml,. preferably between 300 and 1000 ml of liquids. It should be understood, however, that the present invention is also applicable to other absorbent articles such as incontinent briefs, incontinent undergarments, diaper holders and liners and the like.

FIG. 1 shows the absorbent article 1, comprising an absorbent core 3. The absorbent core 3 comprises a perimeter 5 having a front transverse edge 7, a back transverse edge 9 and two longitudinal sides 13,13'. An imaginary transverse center line 15 is located midway between the front transverse edge 7 and the back transverse edge 9 and divides the core 3 into a front half section 17 and a back half section 19. In one embodiment of the absorbent core according to the invention, the amount of absorbent material in the back half section 19 is larger than the amount of absorbent material in the front half section 17. Preferably, the average amount of absorbent material per unit area, or average basis weight, in the back half section 19 is higher than in the front half section 17.

In FIG. 1 the absorbent article, or diaper 1, is shown in its flat-out, uncontracted state (i.e., with elastic induced contraction pulled out) with portions of the article being cutaway to more clearly show the construction of the diaper 1 and with the portion of the diaper 1 which faces or contacts the wearer, the inner surface, oriented towards the viewer. As shown in FIG. 1, the diaper 1 preferably comprises a liquid pervious topsheet 24; a liquid impervious backsheet 26 joined with the topsheet 24; the absorbent structure, or core 3 being positioned between the topsheet 24 and the backsheet 26; elasticized leg cuffs 32,32'; an elastic waist feature 34; and a fastening system generally multiply designated as 36.

The backsheet 26 comprises a front waist edge 39 and a back waist edge 40. A front waist region 58 of the backsheet 26 is located adjacent the front waist edge 39 and a back waist region 58 of the backsheet is located adjacent the back waist edge 40. In the back waist region 56 two cushioning members 33 are located. The cushioning members 33 are isolated from the core 3 such that liquids cannot enter into the cushioning members 33. Thereto, a liquid barrier 35 is located between the perimeter 5 of the core 3 and the cushioning members 33. In FIG. 1, the liquid barrier 35 is formed by a sealing line along which the topsheet 24 and the backsheet 26 are connected in a liquid-impervious manner. Alternatively, the liquid barrier 35 can be formed by a liquid-impermeable coating along the perimeter of the core 3, a liquid-impermeable coating along the perimeter of the cushioning members 33, or can be formed by the outer surface of the cushioning members 33 in case these cushioning members are not made of liquid-absorbent material.

In the front waist region 58 of the backsheet 26, two mechanical fasteners 44 are attached, comprising a plurality of hook-like fastening elements, for instance two patches of VELCRO material. When the diaper 1 is put on a user, the mechanical fasteners 44 engage with the cushioning members 33 which form landing surfaces for the fasteners 44. The mechanical fasteners allow easy application of the absorbent article to the wearer. When the absorbent article is applied to the wearer, first the front and back waist sections 56,58 can be connected around the waist of the wearer by means of the mechanical fasteners. Subsequently, when the diaper is in its desired configuration, the tape fastening system 36 can be closed. The combination of mechanical fasteners 44 and tape fasteners 36 allows the waist sections 56,58 to be maintained in an overlapping position, and prevents shifting or gapping of the waist closure.

In the embodiment of FIG. 1 the topsheet 24 and the backsheet 26 have length and width dimensions generally larger than those of the absorbent core 3. The topsheet 24 and the backsheet 26 extend beyond the perimeter 5 of the absorbent core 3. While the topsheet 24, the backsheet 26, and the absorbent core 3 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715,152, allowed, "Absorbent Article With Dynamic Elastic Waist Feature Having A Predisposed Resilient Flexural Hinge", Kenneth B. Buell et al. filed Jun. 13, 1991; each of which is incorporated herein by reference.

The absorbent core 3 may be any absorbent means which is generally compressible, conformable, non-irritating to the wearer's skin, and capable of absorbing and retaining liquids such as urine and other certain body exudates. The absorbent core 3 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 3 should, however, be compatible with the design loading and the intended use of the diaper 1. Further, the size and absorbent capacity of the absorbent core 3 may be varied to accommodate wearers ranging from infants through adults. The length of the absorbent core along the longitudinal center line is thereto not substantially smaller than about 30 cm. Exemplary absorbent structures for use as the absorbent core 3 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference. A preferred embodiment of the absorbent core 3 has longitudinal dimension, L, of about 60 cm, a back transverse edge 9 of about 30 cm, a front transverse edge 7 of 30 cm and a width along the transverse center line 15 of about 20 cm.

The backsheet 26 is positioned adjacent the garment surface of the absorbent core 3 and is preferably joined thereto by attachment means (not shown) such as those well known in the art. For example, the backsheet 26 may be secured to the absorbent core 3 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 3 from wetting articles which contact the diaper 1 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR821 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 3 (i.e., breathable) while still preventing exudates from passing through the backsheet 26.

The topsheet 24 is positioned adjacent the body surface of the absorbent core 3 and is preferably joined thereto and to the backsheet 26 by attachment means (not shown) such as those well known in the art. Suitable attachment means are described with respect to joining the backsheet 26 to the absorbent core 3. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery and are indirectly joined together by directly joining them to the absorbent core 3 by the attachment means (not shown). In the embodiment of FIG. 1, the topsheet 24 and the backsheet 26 generally have the same dimensions and are co-extensive. However, the topsheet may be of smaller size than the backsheet 26 and need not extend to perimeter of the backsheet. Furthermore, the topsheet 24 may be comprised of several strips which are joined together to form a unitary sheet or may comprise a multilayer topsheet.

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 3. There are a number of manufacturing techniques which may be used to manufacture the topsheet 24. For example, the topsheet 24 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 1 preferably further comprises elasticized leg cuffs 32,32' for providing improved containment of liquids and other body exudates. Each elasticized leg cuff 32,32' may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 1, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff.

The diaper 1 preferably further comprises an elastic waist feature 34 that provides improved fit and containment. The elastic waist feature 34 is that portion or zone of the diaper 1 which is intended to elastically expand and contract to dynamically fit the wearer's waist. The elastic waist feature 34 at least extends longitudinally outwardly from at least one of the transverse edges of the absorbent core 3. Disposable diapers are generally constructed so as to have two elastic waist features, one positioned in the back waist region 56 and one positioned in the front waist region 58, although diapers can be constructed with a single elastic waist feature. This is shown in the embodiment of FIG. 1, wherein the waist feature 34 is only placed in the back waist region 56. Further, while the elastic waist feature or any of its constituent elements can comprise a separate element affixed to the diaper 1, the elastic waist feature, or waistband 34 is preferably constructed as an extension of other elements of the diaper such as the backsheet 26 or the topsheet 24, preferably both the backsheet 26 and the topsheet 24.

The elasticized waistband 34 may be constructed in a number of different configurations including those described in U.S. Pat. No. 4,515,595 issued to Kievit et al. on May 7, 1985 and the above referenced U.S. patent application Ser. No. 07/715,152; each of these references being incorporated herein by reference.

The diaper 1 also comprises a fastening system 36 which forms a side closure which maintains the first waist region 56 and the second waist region 58 in an overlapping configuration such that lateral tensions are maintained around the circumference of the diaper to maintain the diaper on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. B1 4,662, 875 entitled "Absorbent Article" issued to Hirotsu et al. on May 5, 1987; and the hereinbefore referenced U.S. patent application Ser. No. 07/715,152; each of which is incorporated herein by reference.

Figure 2:
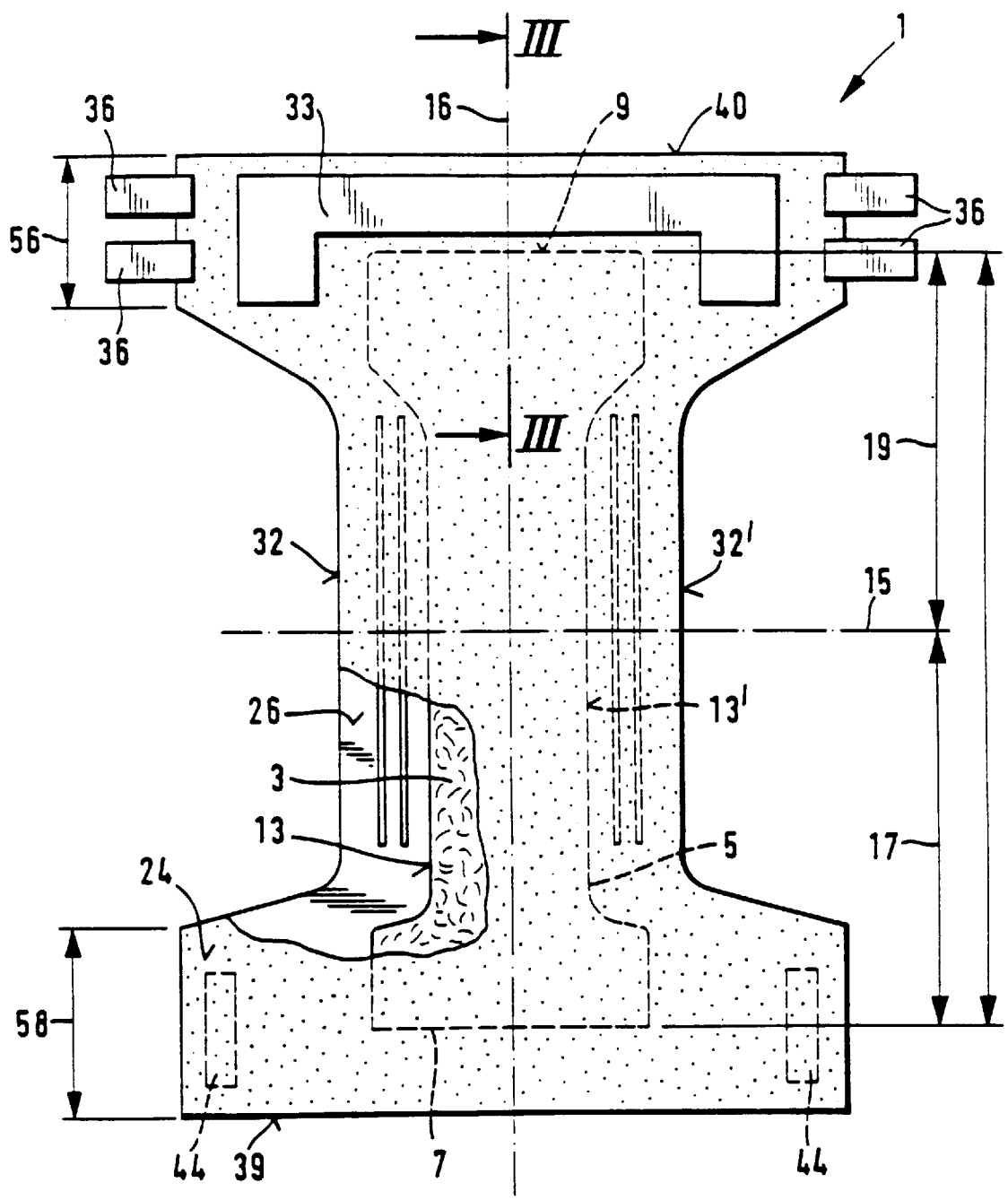
FIG. 2 shows a front elevational view of an absorbent article wherein the cushioning member is parallel to at least a part of the perimeter of the backsheet in the back waist region.

FIG. 2 shows an embodiment of an absorbent article wherein the cushioning member 33 is a single element which extends parallel to at least a part of the perimeter of the backsheet 26. The cushioning member is made of airfelt and is made simultaneously with the core 3 by airlaying of cellulose fibers onto a laydown screen. A process for producing absorbent cores by air lying in described in U.S. Pat. No. 4,765,780 (Angstadt). Such a process only needs a minor modification to produce the absorbent structure according to the invention. After laying down the core 3 and the cushioning member 33, the core and the cushioning member are adhesively attached to the backsheet 26. The fibers of the cushioning member 33 may, prior to affixing the cushioning member between topsheet 24 and the backsheet 26, be treated with a hydrophobic additive or with a liquid-impervious coating to prevent absorption of liquids into the member 33.

Cushioning members 33 can be made of any generally resilient material such as stacked tissues, creped tissue, foamed material, etc. Preferably the cushioning members have a caliper which is larger than the caliper of the core 3 in its wet state.

Figure 3:
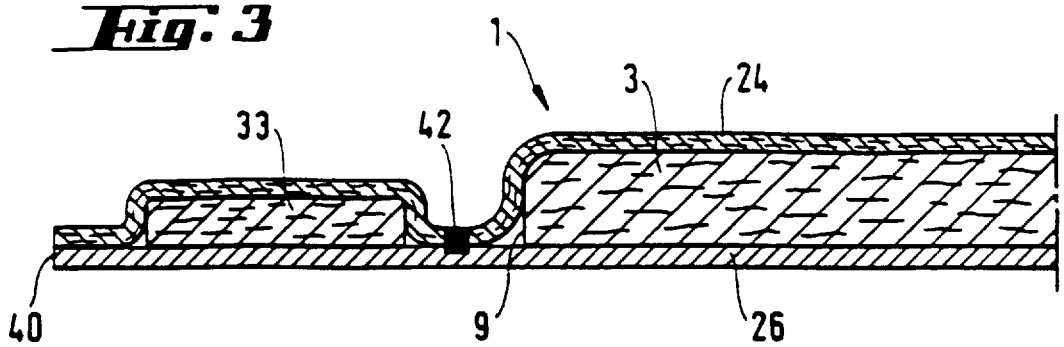
FIG. 3 shows a cross-sectional view of an absorbent article along the longitudinal centerline.

FIG. 3 shows a cross sectional view of a preferred absorbent article 1 wherein the cushioning member 33 is encased between the topsheet 24 and the backsheet 26. The liquid barrier means 35 are formed by a sealing line 42 which comprises a line of adhesive attaching the topsheet to the backsheet. Preferably, the adhesive penetrates into the topsheet such that liquid cannot horizontally wick from the core 3 to the cushioning member 33 through the topsheet 24. However, the topsheet 24 may be of such a structure that no wicking of liquid in the topsheet in the horizontal direction takes place. This will for instance be the case for topsheets which consist of apertured formed thermoplastic films, as described in U.S. Pat. No. 4,629,643 (Curro) or WO92/00050 (Goodman). In such a case, the sealing line 42 connects the topsheet 24 to the backsheet 26 in such a way that no liquids can pass to the cushioning member 33 between the topsheet and the backsheet.

The sealing line 42 may alternatively be formed by a fusion bond between the topsheet and the backsheet or by an ultrasonic bond. Alternatively, an elastic member of the elastic waist band 34 may be comprised between the topsheet and the backsheet in the area of the sealing line 42. In this case, the topsheet is sealingly connected to the backsheet via the elastic member.

Figure 4:
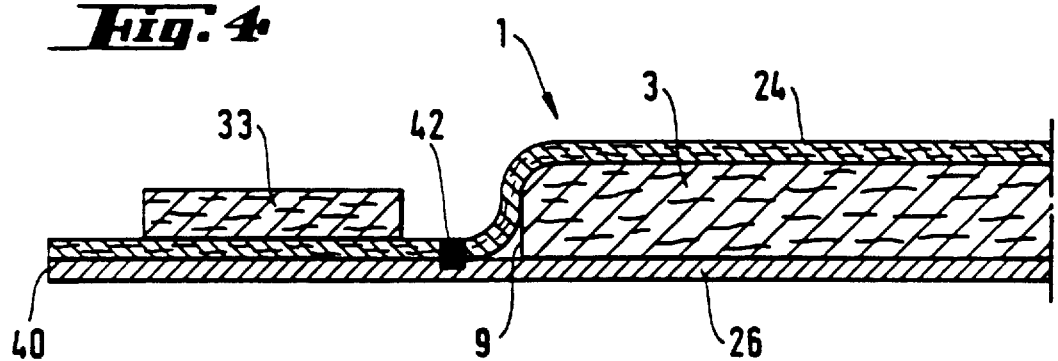
FIG. 4 shows a cross-sectional view of an absorbent article along the longitudinal centerline, the cushioning member being located on the topsheet.

In the embodiment of FIG. 4, the cushioning member 33 is located on top of the topsheet 24. The cushioning member 33 is in this case made of a material such as a resilient foam or a folded tissue, having sufficient integrity to be connected to the absorbent article externally to the topsheet 24. It is in this case also possible that the topsheet 24 terminates at the sealing line 42 and does not extend to the back waist edge 40 of the backsheet 26.

Figure 5:
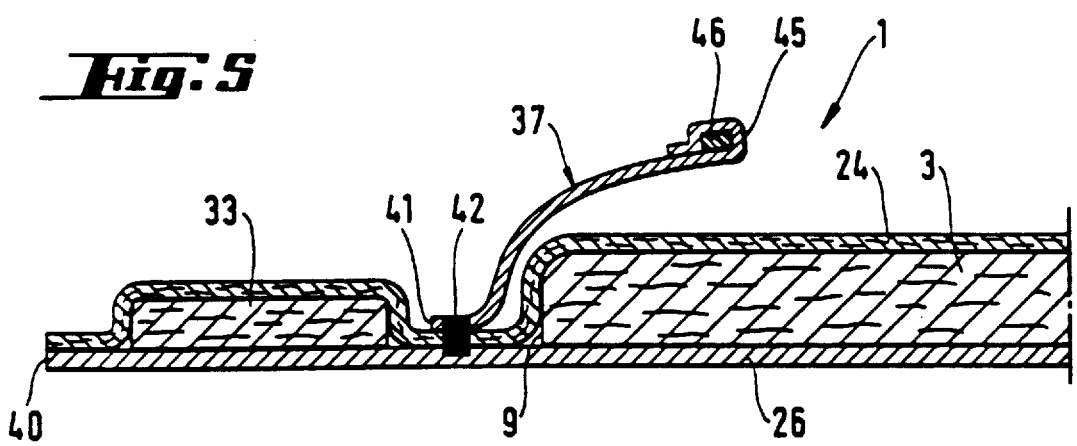
FIG. 5 shows a cross-sectional view of an absorbent article along the longitudinal centerline, the article comprising an elasticated stand-up barrier cuff.

FIG. 5 shows an embodiment of an absorbent structure wherein the liquid barrier 35 comprises a stand-up barrier cuff 37 comprising a proximal edge 41 which is sealingly connected to the topsheet 24. The stand-up barrier cuff comprises a distal edge 45 and elastication means 46 which are connected to the distal edge 45 of the cuff in a pre-stretched manner. The lateral sides of the distal edge 45 are connected to the absorbent article to prevent inversion of the barrier cuff 37. The distal edge 45 is paced away from the topsheet 24 by the contractive force of the elastication means 45. Liquids and other wastes are prevented by the barrier cuff 37 from migrating along the topsheet 24 to the cushioning member 33. The barrier cuff 37 may be breathable or liquid- and vapour impermeable.

Figure 6:
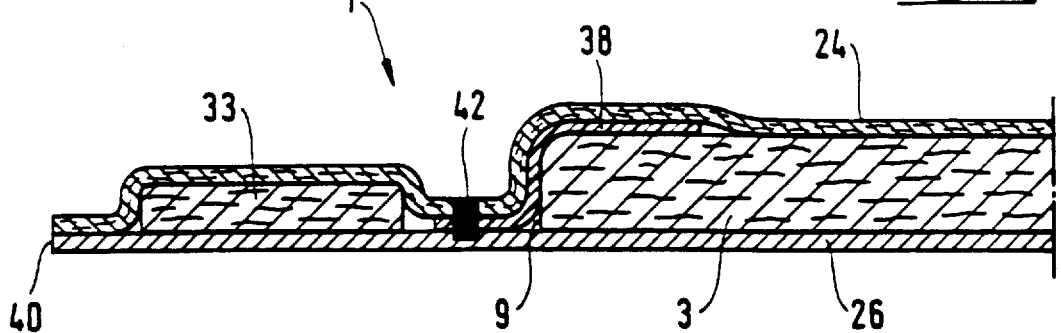
FIG. 6 shows a cross-sectional view of an absorbent article along the longitudinal centerline, a backshield being placed along the back transverse edge of the core.
Figure 7:
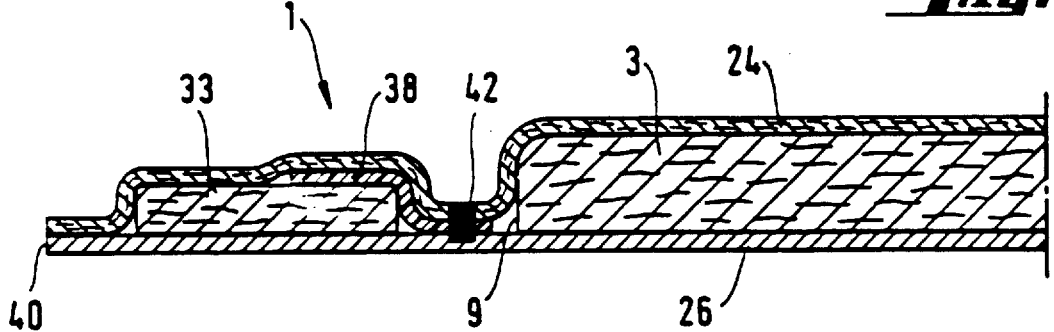
FIG. 7 shows a cross-sectional view of an absorbent article along the longitudinal centerline, a backshield being placed between the back transverse edge of the core and the cushioning member.

In the embodiment of FIG. 6, the liquid barrier 35 is formed by a backshield, or strip, 38 of liquid-impervious material overlying the core 3 along the back transverse edge 9. The strip 38 is glued to the backsheet 26. The strip 38 is preferably formed of liquid-impervious material such as a polyethylene film, but can also be formed by a hydrophobic non-woven material. The strip 38 can also be formed by a coating such as a layer of adhesive. In FIG. 7 it is shown that in an alternative embodiment, the strip 38 overlies the cushioning means 33.

The strip 38 is connected to the backsheet 26 along a sealing line 42, which may be formed by a fusion bond, a glue line or glue spiral or an ultrasonic bond. The strip 38 prevents leakage from the back transverse edge 9 of the core to the back waist edge 40 of the backsheet 26. In an alternative embodiment, the strip 38 may be located on top of the topsheet 24.

Figure 8:
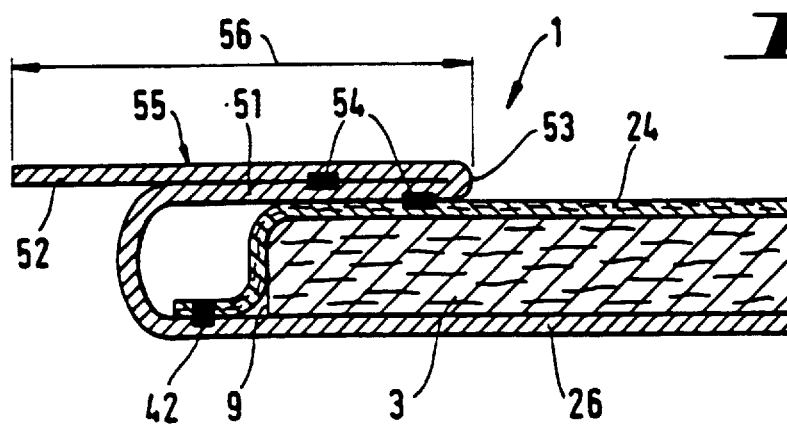
FIG. 8 shows a cross-sectional view of an absorbent article along the longitudinal centerline comprising a z-like fold.

FIG. 8 shows an embodiment wherein the back waist section 56 of the backsheet 26 is doubled over in a z-like fold 55. The back waist section 56 comprises a first part 51 which is folded inwardly onto the topsheet 24 and is attached to the topsheet by fixing means 54 which may be ultrasonically formed bonds, fusion bonds or adhesive bonds. A section part 52 of the back waist section 56 of the backsheet 26 is folded outwardly along foldline 53 and is attached in a doubled-over position to part 51.

FIG. 9 shows an embodiment in which the backsheet 26 is rendered elongatable in the region 48 between the core 3 and the cushioning member 33. The backsheet may have been stretched to impart a permanent elongation thereto. Alternatively, the backsheet 26 may have been contacted by two corrugated members to impart a harmonica-like permanent physical deformation, such as described in U.S. Pat. No's 5,156,793 (Buell) and 5,143,679 (Weber). By allowing the distance between the core 3 and the cushioning members 33 to vary, the core can move to a large extent independently from the cushioning members 33. Hence it is prevented that the movement of the core 3 causes friction of the cushioning members 33 along the back or hips of the user.

Preferable, an elastic member 50 is interposed between the topsheet 24 and the backsheet 26 in the elongatable area 48, as shown in FIG. 10. The elastic member 50 can be connected to the topsheet and backsheet in its relaxed state. Subsequently, the topsheet, backsheet and elastic member 50 may be passed between corrugated members to render the topsheet and backsheet permanently elongatable. The elastic member 50 is unaffected by being passed between the corrugated members. Alternatively, the elastic member 50 may be attached to the topsheet and backsheet in a pre-stretched state, such that topsheet and backsheet are gathered by the contraction of the elastic member. Again, alternatively, the topsheet and backsheet may be gathered, the elastic member 50 being attached in its relaxed state.

In the embodiment of FIG. 11, the back waist section of the absorbent article is formed by a separate section 47 which is attached to the backsheet 26. Preferably, the separate section is formed by an elastic, breathable nonwoven material. Alternatively, the separate section 47 comprises a laminate of an elastic film that is attached in its relaxed state to a non-elastic layer. The laminate can be made elastic in selective areas by permanently elongating the non-elastic film as described above. A laminate useful for forming a separate section 47 is described in International patent application no. PCT/DE 93/01177.

FIG. 12 shows a cross-sectional view of the core 3 along the longitudinal center line 16. Within the core 3, four sections 13a, 13b, 13c and 13d of equal length, L/4, can be considered, the caliper of the core being different in each section. In the embodiment of FIG. 12, the core 3 comprises fluff pulp of a uniform density. The caliper of section 13a is about 7 mm. The caliper in section 13b is about 10 mm, the caliper of section 13c is about 8 mm and the caliper in section 13d is about 5 mm. Hence the ratio of the basis weights of the fibers of combined sections 13a and 13b, which form the back half section of core 3, and combined sections 13c and 13d, which form the front half section, is about 1.3.

The core 3 may comprise cellulosic fibers, synthetic fibers such as crimped polyester fibers, mixtures of synthetic and cellulosic fibers or absorbent foam material as described in U.S. Pat. No. 5,268,224 (Desmarais). The caliper of the core 3 as shown if FIG. 12 can be made uniform by calendering. This is illustrated in FIG. 13. The core 3 of FIG. 13 comprises areas of relatively high density in the back half section 13a, 13b and a relatively low density in the front half section 13c, 13d. The density of the fibrous or foamed absorbent material in the front and back half sections may range from 0.1 to 1 $g/cm^3$. The density in each section is proportional to the caliper before calendering to a uniform caliper. The increased density of the fibers in the back half section improves retention of liquids in that section as the smaller interfiber capillaries will exert a higher suction on liquids in the back half section.

The core 3 in FIGS. 14 and 15 comprises a water-insoluble, absorbent gelling material, which swells upon contact with liquids to form a hydrogel. Such materials are described in detail in U.S. Pat. No. Re. 32,649 (Brandt) and can absorb at least 20 times their own weight of liquid. The hydrogel material may be in particulate form, particle sizes ranging from 10 micrometers to 2000 micrometers or can come in the form of flakes, fibers or sheets. The hydrogel material may also be comprised of an interpartically crosslinked aggregate as described in U.S. Pat. No. 5,102, 597 (Roe). The core 3 in FIG. 14 comprises a lower layer 63, which is substantially free of absorbent gelling material or which contains small size absorbent gelling material particles or absorbent gelling material fines, as described in EP-A-0 567 738 (Plischke). The lower layer 63 serves to contain the absorbent gelling material in the upper layer 64 and to prevent the absorbent gelling material particles from contacting the backsheet and hence cause surface irregularities on the backsheet (so called "pock marking") and to prevent the absorbent gelling material from perforating the backsheet.

In the absorbent core of FIG. 14, the absorbent gelling material is uniformly dispersed through the thickness, W, of each region 13a–13d of the layer 64. However, the absorbent gelling material may be present in different concentrations throughout the thickness of layer 64 of the core 3, and may be highest in the parts of the core that are furthest away from the wearer (those parts of layer 64 that are located closest to layer 63). Such cores with a so-called absorbent gelling material "gradient" are described in detail in EP-A-0 198 683 (Duenk).

In the embodiment of FIG. 14, the basis weight of the absorbent gelling material in section 13a is about 0.012 g/cm$^2$, the basis weight in section 13b being about 0.016 g/cm$^2$, the basis weight in section 13c being about 0.012 g/cm$^2$ and the basis weight in section 13d being about 0.008 g/cm$^2$ In a preferred embodiment, section 13a contains about 25%, and section 13b contains about 35% by weight of the total amount of absorbent gelling material present in the layer 64. Section 13c may contain about 25% and section 13d about 5% of the total weight of absorbent gelling material in layer 64.

Preferably, the absorbent gelling materials are "high gel strength" materials. High gel strength absorbent gelling material particles will undergo relatively little deformation upon being wetted such that the gelling material does not flow into the capillary void space of the fibrous material and causes undesired gel blocking. Suitable absorbent gelling materials have Gel Layer Permeability (GLP) values higher than $4 \times 10^{-7}$ cm$^3$/s/g. The GLP value can be measured by the method as described in European Application No. 93309614.1.

In the embodiment of FIG. 14, the basis weight of the fibrous or foamed absorbent material is equal for the sections 13a–13d in layer 64. The basis weight of the fibrous or foamed absorbent material may typically be about 0.05 g/m$^2$. However, in addition to a varying basis weight of the absorbent gelling material for each section 13a–13d, the basis weight of the fibrous or foamed absorbent material may also vary in each region 13a–13d, as shown in FIG. 15. Again, the core 3 as shown in FIG. 15 can be calendered to a uniform caliper.

Figure 16:
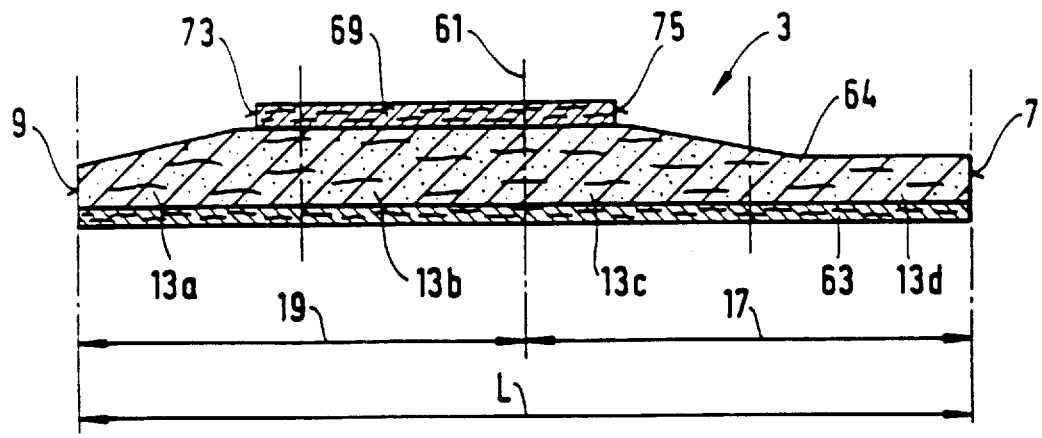
FIG. 16 shows a cross-sectional view of the core of the absorbent article along the longitudinal centerline, the core comprising an acquisition/distribution layer.

In FIG. 16 an embodiment of an absorbent core 3 is shown that comprises an acquisition/distribution layer 69, located on top of the layer 64 of core 3. The acquisition/distribution layer serves to quickly collect large gushes of liquids and to isolate these from the body of the wearer until these liquids have been absorbed in the underlying layer 64. The density of the acquisition/distribution layer is preferably between 0.03 and 0.13 g/cm$^3$ the basis weight being between 100 and 500 g/m$^2$, depending on the volume of the gush that is to be taken up. A preferred material for the acquisition/distribution layer 69 is chemically stiffened cellulose material as described in EP-A-0 429 112 (Herron) U.S. Pat. No. 4,898,642 (Moore) and 4,889,597 (Bourbon). Further useful acquisition/distribution layers comprise open networks of thermally bonded synthetic fibers as described in U.S. application Ser. No. 08/141,156 and EP-A-513 148.

An important property of the acquisition/distribution layer 69 is its ability to maintain a sufficient void volume for liquid uptake, even when wet. The fibers in the layer 69 should be sufficiently resilient to not collapse in their wet state upon compression. It was found that layers having a wet compressibility of at least 5 cm$^3$g$^{-1}$ and a drip capacity of at least 10 g g$^{-1}$ can be successfully used in acquisition/distribution layer 69.

The wet compressibility and the drip capacity can be measured by the test described below. All tests are carried out at about 23°±2° C. and at 50±10% relative humidity. The specific synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na$_2$SO$_4$; 0.85 g/l of (NH$_4$)H$_2$PO$_4$; 0.15 g/l (NH$_4$)H$_2$PO$_4$; 0.19 g/l of CaCl$_2$; ad 0.23 g/l of MgCl$_2$. All of the chemicals are of reagent grade. The pH of the synthetic Urine is in the range of 6.0 to 6.4.

Sample Pad Preparation for Wet Compressibility and Drip Capacity Tests

The sample pads are prepared using a padmaker machine of type such as is described below or an equivalent machine, which provides a consistent and homogeneous laydown of fluff. Four 30 g portions of dry fluff (or equivalent material, for example chemically cross-linked cellulose) are weighed out. A ply of tissue porous enough for air to pass through it while retaining fluff on it, is cut to 36.8 cm×36.8 cm (14.5"×14.5"), and is placed evenly on a forming screen of an air laid felt padmaker machine. The tissue completely covers the forming screen and is made to curve up at its sides to prevent escape of the fluff. The tissue forms the bottom of the pad. The vacuum chamber motor and compressed air supply on the padmaker machine are turned on. One 30 g portion of fluff is added to the sample chamber on the padmaker machine in small amounts via a sample feed and without obstructing the blades of the machine. Compressed air is circulated vigorously in the chamber to expedite separation and passage of the fibres through a plexiglass cylinder and the prismoid column to the forming screen.

The vacuum is turned off and the forming screen is pulled out of the padmaker machine and rotated through a quarter turn in the clockwise direction. The screen is returned to the padmaker machine. Another 30 g portion of fluff is added to the chamber on the machine and the above procedure is repeated. Fluff is added in the same manner until all four portions have been transferred to the forming screen. The forming screen, and the pad formed thereon, is then removed from the padmaker machine, and the pad is carefully transferred from the screen to a piece of cardboard, or similar smooth flat surface. A second ply of tissue is added to the top of the pad, and a second piece of cardboard placed on top of that.

A steel weight having dimensions of around 35.6 cm×35.6 cm×2.5 cm (14"×14"×1") having a weight of around 16.3 kg (36 lbs) is placed on top of the pad for approximately 120 seconds, or longer until the pad is needed. The weight is then removed and the pad is pressed by application of a force of around 4,500 kg (10,000 lbs) on a large Carver press to improve pad integrity. The pad is removed from the press and trimmed on a paper cutter to have dimensions around 30.5 cm×30.5 cm (12"×12"), and is then further cut according to the size required by the particular test in which it is to be used.

The use of a padmaker machine to form the sample pads is not intended to be limiting. Any suitable method can be used provided a consistent and homogeneous laydown of fluff is achieved, which is then compressed under the above conditions to give a pad having substantially the same density and basis weight as achieved above.

Wet Compressibility Test

This test is designed to measure the volume of a pad of fibrous material under varying load conditions when wet. The objective is to measure the fibrous material's resistance to load by measuring the volume maintained under that load.

A fluff test pad is prepared as described above. Any tissue present on the surfaces of the pad is removed. The pad is then densified under a 3.6 kg cm$^{-2}$ (51 psi) load for pad integrity reasons using a Carver laboratory press. The thickness of the pad is measured and its fibre density calculated by pad weight÷(pad thickness×pad area).

The dry weight of the pad is multiplied by 10, and this represents the target wet weight on loading. The dry pad is transferred onto a top loading balance having a 0.01 g sensitivity. Synthetic urine is dispensed slowly onto the pad until the target wet weight is achieved as measured by the balance. The wet pad is carefully transferred onto the surface of a compressibility tester of the Buckeye design, and a weight having substantially the same area as the pad (about 10.2 cm×10.2 cm) and corresponding to a pressure of 77 g cm$^{-2}$ (1.1 psi) is lowered slowly onto the pad. The pad is left for 60 seconds to allow it to equilibrate under the load, and then the thickness of the compressed pad is recorded using calipers. The Wet Compressibility is the void volume per gram of dry fluff and is calculated as follows:

Void Volume (cm$^3$) = Total Volume − Fibre Volume =

(pad thickness under load (cm) × pad area (cm$^2$)) −

(pad dry weight (g)/fibre density (g cm$^3$)

Wet Compressibility = Void volume per gram =

[(pad thickness under load (cm) × pad area (cm$^2$)) −

(pad dry wt. (g) /fibre density g cm$^{-3}$)] ÷ pad dry wt. (g)

where fibre density is calculated from the initial pad weight and thickness measurements (i.e. under no load conditions).

Drip Capacity Test

A sample pad prepared as described above is cut on a paper cutter to have dimensions 7.5 cm×7.5 cm. The pad is weighed and is placed on a large mesh wire screen which is in turn positioned on a drip tray. The whole apparatus is then mounted on a top-loading balance.

Synthetic urine is introduced via a pump (Model 7520-00, as supplied by Cole-Parmer Instruments Company, Chicago, U.S.A) into the centre of the sample pad at a rate of 5±0.25 ml s$^{-1}$. The time for the pad to release the first drop of synthetic urine through the bottom of the pad and into the drip tray is recorded. The pump is immediately stopped as soon as this occurs. The time recorded and the pumping rate are then used to calculate the volume (ml) of synthetic urine absorbed by the sample on reaching saturation, i.e. when the sample starts to drip. The balance can be used to check this periodically, thereby minimising any variation in the pump delivering the synthetic urine. This is known as the Drip Capacity, and is given as the ratio:

{Urine retained by sample pad on saturation (ml)}/{Dry Weight of sample (g)}

Figure 17:
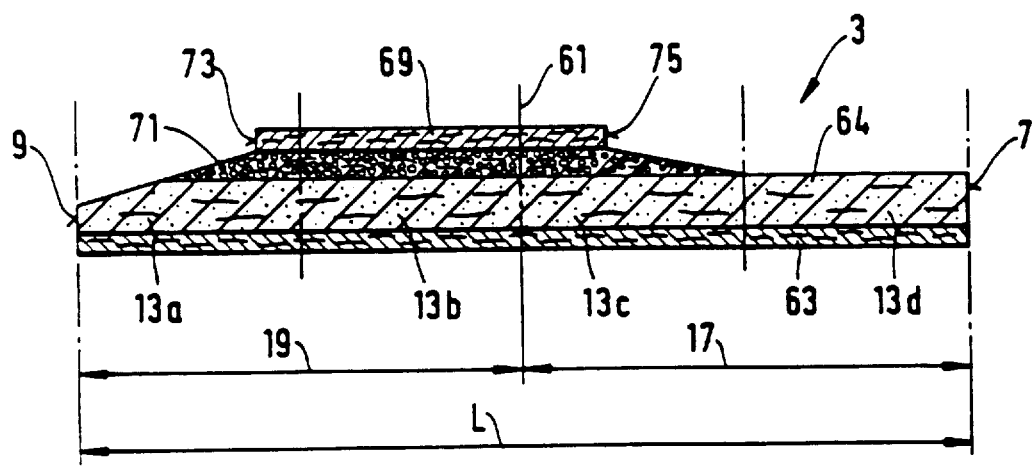
FIG. 17 shows a cross-sectional view of the core of the absorbent article along the longitudinal centerline, the core comprising an acquisition/distribution layer, FIG. 18 schematically shows the region of the core for measuring the average basis capacity of the core, FIG. 19 schematically shows the test equipment for measuring the average basis capacity of an absorbent core, and FIG. 20 schematically shows the test equipment for measuring the run-off of liquid via the back transverse edge of the core.

In the embodiment of FIGS. 16 and 17, the acquisition/distribution layer 69 is of generally rectangular shape and comprises a back edge 73 and a front edge 75. The distance between the back edge 73 of the acquisition/distribution layer 69 and the cross sectional center line 61 is larger than the distance between the front edge 75 and the cross-sectional center line. For irregularly shaped acquisition/distribution layers 69, the surface area of the part of the acquisition/distribution layer 69 located between the transverse center line 15 and the back edge 9 of the core 3 is larger than the surface area of the acquisition/distribution layer 69 located between the transverse center line 15 and the front edge 7 of the core 3. Preferably the ratio of the total weight of absorbent material in the acquisition/distribution layer located in the back half section of the absorbent core 3 and located in the front half section of the acquisition-distribution layer is between 1.1 to 3.

In the embodiment of FIG. 17, an extra layer 71 of absorbent gelling material is located underneath the acquisition/distribution layer 69. This layer of absorbent gelling material serves to quickly drain the layer 69, such that it is ready for subsequent gushes of liquid, and maintains a dry buffer adjacent the skin of the wearer. Absorbent gelling materials of high gel strength as mentioned above are suitable to use in the layer 71, as they maintain a relatively open structure through which liquids can pass to the underlying layer 64 without adverse effects of gel blocking. The absorbent gelling material in layer 71 may be mixed with the fibers in the upper part of the layer 64, and may be introduced in this layer during the airlaying of the fibers of the layer 64, using a powder spray nozzle as described in EP-B-0 330 675.

Alternatively, the layer 71 contains a layer of absorbent gelling material which is not substantially mixed with the fibrous or foamed absorbent material of the layer 64. Such a layer of absorbent gelling material may be bonded to a tissue by means of adhesive or frictional forces, as disclosed in U.S. Pat. No. 4,600,458 (Kramer) or may contain a single layer of loose absorbent gelling material particles. Alternatively, the layer 71 comprises a layer of interparticle-crosslinked particles which form a porous macroscopic aggregate as described in U.S. Pat. No's 5,102,597 (Roe) and 5,180,622 (Berg).

When the layers 71 contain a substantially pure layer of absorbent gelling material, it is important that the layer 71 remains permeable for liquids. It was found that absorbent gelling materials having a Gel Layer Permeability of at least 4×10$^{-7}$ cm$^3$/s/g can advantageously be used in the layer 71. The GLP value is an indication of the ability of the absorbent gelling material to maintain a permeable structure and to allow liquid transport through the absorbent gelling material layer, even when wet. The test for measuring the GLP values has been described in detail in European application no. 93309614.1. Alternatively, the absorbent gelling material has an absorption against pressure value (AAP) of at least 23 g/g at a confining pressure of 5 kPa (0.7 psi). A test for measuring the AAP-values has been described in European patent application no. 93909614.1.

For determining the weight of absorbent gelling material in the embodiment of FIG. 17, in the front half and back half sections 17 and 19, the total weight of absorbent gelling material in each section comprises the absorbent gelling material present in both layers 71 and 64. The regions 13a and 13b each contain about 20% by weight the absorbent gelling material in the core 3, regions 13c and 13d each contain 15% by weight and layer 71 contains 30% of the total weight of absorbent gelling material in layers 64 and 71. The absorbent gelling material in the layer 71 need not have the same chemical or physical or physical properties as the absorbent gelling material in the layer 64, but can for instance have a slower absorption speed or a lower absorption under pressure.

Figure 18:
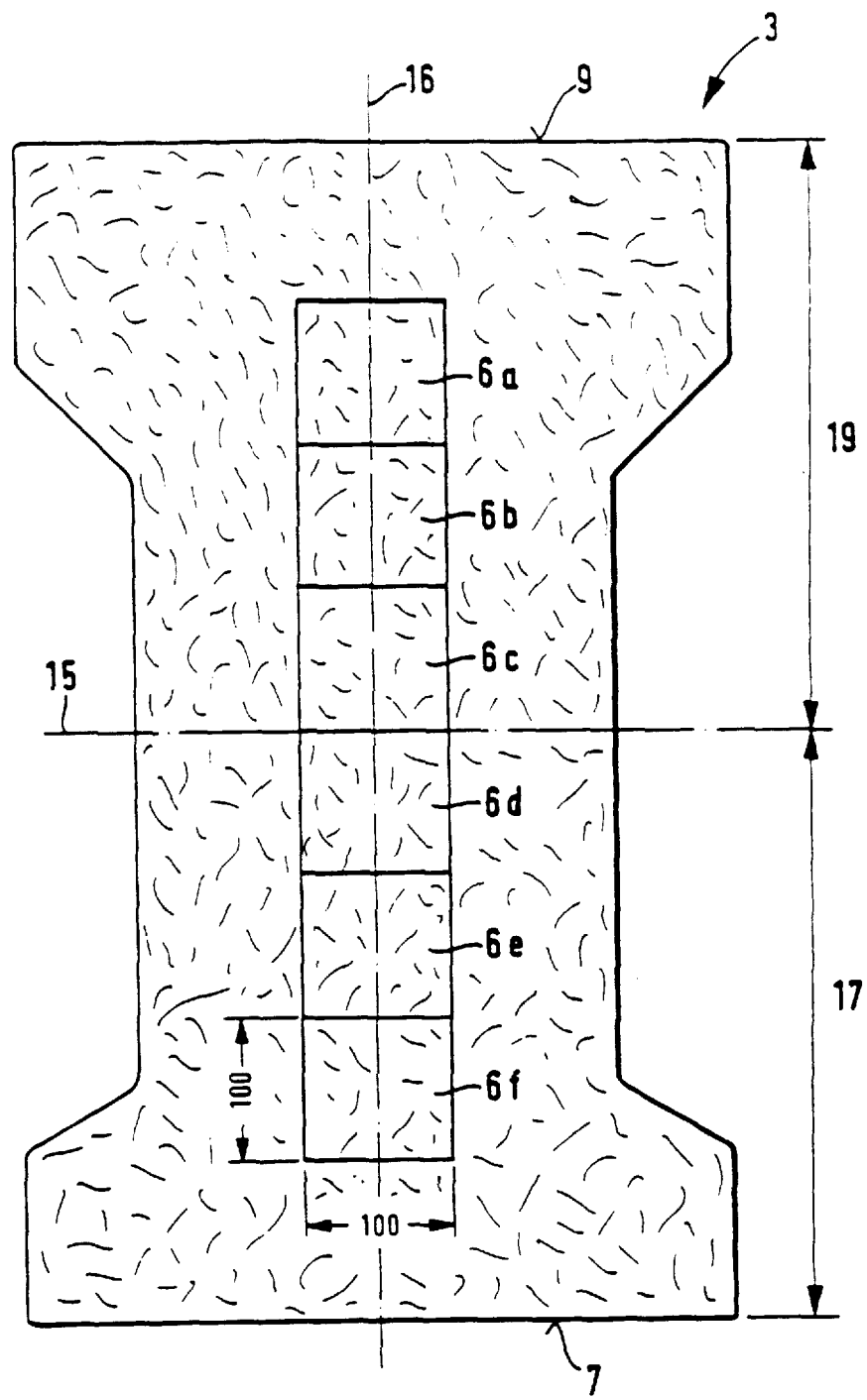

In the following example, the rewet properties of a product having an absorbent core comprising a back half section having a high average basis capacity will be determined and will be compared with the rewet properties of similar products which do not have a majority of the absorbent gelling material located in the back half section. Thereafter, the effect of the liquid barrier means will be measured in a run-off test. The determination of the average basis capacity, the rewet test and the run-off test are described here below:

Average Basis Capacity:

The average basis capacity measures the amounts of liquid absorbed per gram of absorbent material in the central area of the absorbent structure, as indicated in FIG. 18.

First the average basis weight of the material in the central area $6a$–$6f$ is determined in accordance with "Prüfmethode Nr. 1/93 MDS-HI Teil 1; Bestimmung der Flüssigkeitsaufnahme". The absorbent product is laid flat on a surface and the transverse center line 15 that is located midway between the front transverse edge 7 and the back transverse edge 9 and that divides the absorbent core into the front half section 17 and back half section 19, is marked. Likewise the longitudinal center line 16 is marked. A total of up to six test samples $6a$–$6f$ each of 100×100 mm size are labelled and cut out of the absorbent product as detailed in FIG. 18. In case of smaller product size, the number of samples can be reduced. In any case, the samples are taken symmetrically around the transverse center line 15.

Typically each sample $6a$–$6f$ will be composed of absorbent material located between and contained by a nonwoven topsheet 24 and a water impervious backsheet 26 or outer material. The samples $6a$–$6f$ are symmetrically removed about the transverse center line above and below the transverse center line. The labelled samples are removed with the aid of a die or laboratory cutter and are weighed with a laboratory balance to an accuracy of 0.05 gram. For each sample the dry weight, $W_i$, is recorded.

The samples are placed, one at a time, in a metallic meshed basket 81 as illustrated in FIG. 19 with the water impervious backsheet 26 or backing material placed upwards. A perspex plate 82 is placed on top of the sample and the metallic meshed basket 81 is submerged in Jayco synthetic urine which so that the sample and perspex plate 82 are fully submerged for a period of 20 minutes. After 20 minutes, the basket containing the sample is immediately removed and placed on a stand that allows excess test solution to readily drain away. Immediately a 10 kg weight is placed on top of the perspex plate lying on top of the sample for a period of 2 minutes such that a pressure of 100 g/cm$^2$ is exerted on the sample. After the 2 minutes the weight and perspex plate are immediately removed and the sample is immediately weighed. The weight of each sample loaded with liquid, $Wl_i$, is recorded.

The average basis capacity (g/g) for the front half section is given by:

$$1/3 \sum_i [(Wl_i - W_i)/W_i] \quad \text{[for samples } i = 6d, 6e, 6f\text{]}$$

Similarly, the average basis capacity can be determined for the back half section on the basis of samples $6a$, $6b$ and $6c$.

Rewet Test

In the rewet test the ability of an absorbent product to retain absorbed liquids inside the core, is measured. In the rewet test, an absorbent diaper is selected, weighed and the elastic components are either cut in half or removed to allow the product to be laid out in its flattened position. Front and back loading points for application of a test solution are clearly marked on the absorbent product. The front loading point is located on the longitudinal center line 16 at a distance 10 cm from the front transverse edge 7 inwards towards the transverse center line 15. The back loading point is located on the longitudinal center line 16 at a distance 15 cm from the back transverse edge 9 inwards towards the transverse center line 15.

In separate tests, either the front or the back loading point is selected and a volume typical of in in-use conditions of 240 ml of Jayco synthetic urine, of chemical composition as described in the text above, is dripped onto the loading point at a rate of 17 ml/sec. A circular weight of 10 Kg and having a diameter of 16 cm and exerting a loading pressure of 50 g/cm$^2$ (0.7 psi), is placed onto the center of the loading point for a period of 30 minutes. After 30 minutes the weight is carefully removed and dried and eight (8) layers of pre-weighed filter papers (Eaton Dikeman 631, Nr 5) are immediately placed central onto the loading point and the weight gently lowered, without delay, onto the filter paper for exactly 30 seconds. The weight and filter paper are immediately removed on completion of the 30 seconds and the difference in filter paper weight is recorded as the first rewet value. A second set of eight (8) layers of pre-weighed filter papers are immediately placed central onto the loading point and the weight gently lowered, without delay, onto the filter paper for exactly 30 seconds. The weight and filter paper are immediately removed on completion of the 30 seconds and the difference in filter paper weight is recorded as the second rewet value. The total rewet is the sum of the two individual rewet values, i.e. rewet=1st+2nd rewet values.

Run-off test

The run-off test method is utilised to test the effectiveness of a barrier means such as a backshield 38 as shown in FIGS. 7 and 8. The test simulates in use conditions typical for incontinence sufferers in a night time or lying situation where the absorbent material located in the back half of the product under either a large or repeated loading(s) becomes saturated potentially leading to leakage. The mechanism of such leakage can be either through pressure extrusion (via body movement) or simple capillary action whereby urine not adequately restrained within the core region is absorbed by the users clothing or bedding.

The test is performed using an apparatus as detailed in FIG. 20. The absorbent product is selected and the leg elastics are either cut or removed to facilitate flat placement of the product on a working surface. The loading point 85, located along the product's longitudinal center line 16 at a distance of 10 cm from the back transverse edge 9 of the core 3, is marked on the absorbent product.

The absorbent test product 1 is then laid flat and clamped onto a support 83 which is mounted on an adjustable height platform 84 at an angle of 45% to the platform 84. A stack of 10 sheets of doubled over (150 cm×12.5 cm) bounty ( P & G USA) absorbent towel 86, weighing about 37 grams, is placed in the back waist region 58 of the absorbent product 1 at a distance of 8 mm from the back transverse edge 9 of the core 3. A volume of 250 ml of Jayco Synthetic Urine of composition as detailed above, is added to a dispensing flask 87. The full 250 ml volume of synthetic urine is dispensed onto the test product from a height of 5 mm above the loading point 85 at a rate of 40 ml/min so as to simulate a single heavy loading gush.

Synthetic urine not adequately acquired and absorbed in the time available by the absorbent core 3 is typically extruded under the combined force of gravity and/or through capillary action and is collected by the stack of absorbent towels 86 or is contained by the waist barrier 38. The tissues 86 are weighed both prior to and after an elapsed time period of 5 minutes following the cessation of the gush. The difference is recorded as run-off.

Comparative Example I:

In this example three incontinence briefs, or diapers, were wetted in the front and back half sections and the rewet values were measured in each section. The average basis capacity of the back half section and the front half section of each sample was determined by the method described above. The samples are similar in terms of their dimensions and capacity and are representative of absorbent products typically in use for adult heavy incontinence sufferers. The following three products are compared:

1) An incontinence brief having an absorbent core according to the invention, for the user size group 'Medium'.
2) A incontinence brief otherwise identical to 1) but with a absorbent core comprising more absorbent gelling material in the front half section than in the back half section, and
3) A commercially available incontinence brief sold under the trade name Tena Slip Super (Art. No. 711200, manufacturer Mölnlycke AB) in the user size group 'Medium'.

Results of the rewet test and absorbent capacity measurements of the above products are given in Table I below.

From Table I it can be seen that for sample 1, which has in the back half section a larger amount of absorbent gelling material and a higher average basis capacity, the rewet in the back half section is smaller by about a factor 10 compared to the rewet of samples 2 and 3. Because of the low rewet values in the back half section, the samples 1 are especially adapted for use by bedridden users, in combination with the cushioning members 33. In the lying down position, the liquid will be stored predominantly in the back half section of the core. Maintaining the rewet at an as low as possible level is especially important with bedridden users to avoid a negative impact on the skin of wetness and pressures which normally occur with incontinent bedridden users.

TABLE I

Comparison of the average basis capacity and rewet values in the front half section and back half section for three adult incontinence products.

| Parameter | Sample 1 Absorbent gelling material predominately in back half section | Sample 2 Absorbent gelling material predominately in front half section | Sample 3 Commercially available product |
|---|---|---|---|
| Product Dimensions | | | |
| Product Length (mm) | 838 | 838 | 805 |
| Product Width front (mm) | 625 | 625 | 650 |
| Product Width back (mm) | 637 | 637 | 634 |
| Absorbent Structure | | | |
| Core Length (mm) | 651 | 651 | 636 |
| Core width Centre (15) (mm) | 200 | 200 | 175 |
| Core Width Back (9) (mm) | 325 | 325 | 330 |
| Core Width Front (7) (mm) | 325 | 325 | 325 |
| Total Core Area (sccm) | 1597 | 1597 | 1580 (±60) |
| Total Core Weight (g) | 103 | 103 | 110 (±5) |
| Front Half Section | | | |
| Airfelt/Fibrous Material | | | |
| Area (sqcm) | 764 | 764 | 754 (±50) |
| Weight (g) | 43.5 | 43.5 | 46 (±3) |
| Basis Weigh (g/sqcm) | 0.056 | 0.056 | 0.062 |
| Absorbent Gel Material | | | |
| Area (sqcm) | 495 | 495 | 754 |
| Weight (g) | 4.5 | 7.5 | 6 (±0.5) |
| Basis Weight (g/sqcm) | 0.0091 | 0.015 | 0.008 |
| Test Results Front Half | | | |
| Average Basis Capacity (g/g) | 9.2 | 10.9 | 8.6 |
| Rewet (g) | 1.6 | 0.19 | 2.7 |
| Back Half Section | | | |

TABLE I-continued

Comparison of the average basis capacity and rewet values in the front half section and back half section for three adult incontinence products.

| Parameter | Sample 1 Absorbent gelling material predominately in back half section | Sample 2 Absorbent gelling material predominately in front half section | Sample 3 Commercially available product |
|---|---|---|---|
| Airfelt/Fibrous Material | | | |
| Area (sqcm) | 833 | 833 | 826 |
| Weight (g) | 47.5 | 47.5 | 51 (±3) |
| Basis Weigh (g/sqcm) | 0.056 | 0.056 | 0.062 |
| Absorbent Gel Material | | | |
| Area (sqcm) | 495 | 495 | 826 |
| Weight (g) | 7.5 | 4.5 | 6 (±0.5) |
| Basis weight (g/sqcm) | 0.015 | 0.091 | 0.0073 |
| Test Results Back Half | | | |
| Average Basis Capacity (g/g) | 10.9 | 9.2 | 8.6 |
| Rewet (g) | 0.17 | 1.6 | 2.8 |

Comparative Example II

In the following comparative example, three products, indicated as sample 4, sample 5 and sample 6 in Table II, are compared. Sample 4 is a product similar to sample 1 in the first comparative example, but is provided with liquid barrier means of the type depicted in FIG. 7. Sample 5 is a product identical to sample 1 in comparative example I and Sample 6 is a product identical to sample 3 in comparative example I. From table II it can be seen from sample 5 and sample 6 that the liquid run-off is reduced by about a factor 2 by the presence of an increased amount of absorbent material in the back half section. However, the amount of absorbent gelling material cannot be increased at will, as at higher concentrations gel blocking will occur. Also for cost reasons, the amount of absorbent gelling material in the back half section cannot be increased at will. As shown by sample 4, the addition of a liquid barrier means can further reduce the run off to a negligible level. Reduction of the leakage at the back waist section of the absorbent product is especially important for those products comprising cushioning members 33, which products are used by bedridden patients for whom the combination of pressure and wetness can lead to a detrimental skin condition.

TABLE II

Comparison of the run-off values for three adult incontinence products.

| Parameter | Sample 4 Absorbent gelling material predominately in back half section with waistshield | Sample 5 Absorbent gelling material predominately in back half section without waistshield | Sample 6 Commercially available product without waistshield |
|---|---|---|---|
| Product Dimensions | | | |
| Product Length (mm) | 838 | 838 | 805 |
| Product Width front (mm) | 625 | 625 | 650 |
| Product Width back (mm) | 637 | 637 | 634 |
| Absorbent Structure | | | |
| Core Length (mm) | 651 | 651 | 636 |
| Core width Centre (15) (mm) | 200 | 200 | 175 |
| Core Width Back (9) (mm) | 325 | 325 | 330 |
| Core Width Front (7) (mm) | 325 | 325 | 325 |
| Total Core Area (sqm) | 1597 | 1597 | 1580 (±60) |
| Total Core Weight (g) | 103 | 103 | 110 (±5) |
| Front Half Section | | | |
| Airfelt/Fibrous Material | | | |
| Area (sqcm) | 764 | 764 | 54 (±50) |
| Weight (g) | 43.5 | 43.5 | 46 (±3) |
| Basis Weigh (g/sqcm) | 0.056 | 0.056 | 0.062 |
| Absorbent Gel Material | | | |
| Area (sqcm) | 495 | 495 | 754 |
| Weight (g) | 4.5 | 4.5 | 6 (±0.5) |
| Basis Weight (g/sqcm) | 0.0091 | 0.0091 | 0.008 |

TABLE II-continued

Comparison of the run-off values for three adult incontinence products.

| Parameter | Sample 4 Absorbent gelling material predominately in back half section with waistshield | Sample 5 Absorbent gelling material predominately in back half section without waistshield | Sample 6 Commercially available product without waistshield |
|---|---|---|---|
| Test Results Front Half | | | |
| Average Basis Capacity (g/g) Back Half Section | 9.2 | 9.2 | 8.6 |
| Airfelt/Fibrous Material | | | |
| Area (sqcm) | 833 | 833 | 826 |
| Weight (g) | 47.5 | 47.5 | 51 (±3) |
| Basis Weigh (g/sqcm) | 0.056 | 0.056 | 0.062 |
| Absorbent Gel Material | | | |
| Area (sqcm) | 495 | 495 | 826 |
| Weight (g) | 7.5 | 7.5 | 6 (±0.5) |
| Basis Weight (g/sqcm) | 0.015 | 0.015 | 0.0073 |
| Test Results Back Half | | | |
| Average Basis Capacity (g/g) | 10.9 | 10.9 | 8.6 |
| Run-Off (g) | zero | 17.5 | 33.6 |

What is claimed is:

1. An absorbent article comprising:
   a liquid pervious topsheet,
   a liquid impervious backsheet having a perimeter comprising a front waist edge and a back waist edge, and a front waist region adjacent the front waist edge and a back waist region adjacent the back waist edge,
   an absorbent core interposed between said topsheet and said backsheet, said absorbent core having a perimeter comprising a back transverse edge, a front transverse edge and two longitudinal sides,
   a cushioning member positioned between the perimeter of the backsheet and the perimeter of the absorbent core in at least said back waist region for distribution of pressure on a user in a lying down position, and
   a liquid barrier between said absorbent core and said cushioning member for substantially preventing liquid transport from said absorbent core to said cushioning member.

2. The absorbent article of claim 1 wherein said cushioning member comprises airfelt.

3. The absorbent article of claim 1 wherein said cushioning member is located adjacent at least a portion of one of said longitudinal sides of said absorbent core.

4. The absorbent article of claim 3 wherein cushioning member has a surface area of at least 25 square centimeters.

5. The absorbent article of claim 1 wherein said cushioning member extends generally parallel to at least a part of said perimeter of said backsheet.

6. The absorbent article of claim 1 wherein said liquid barrier comprises a liquid-tight sealing area formed at a juncture of said topsheet and said backsheet.

7. The absorbent article of claim 1, said backsheet further having a user-facing side and a garment-facing side, wherein said cushioning member is positioned adjacent said garment-facing side of said backsheet.

8. The absorbent article of claim 7 wherein said liquid barrier comprises said backsheet.

9. The absorbent article of claim 1, said backsheet further having a user-facing side and a garment-facing side, and the absorbent article further comprising at least two mechanical fasteners joined to the garment-facing side of said backsheet in said front waist region for engaging said cushioning member upon use of the absorbent article.

10. The absorbent article of claim 1, said backsheet further having a portion which extends beyond said back transverse edge of said absorbent core wherein at least said portion of said backsheet is a breathable material.

11. The absorbent article of claim 1 wherein said backsheet is extensible in an area between said absorbent core and said cushioning member to allow spacing between said cushioning member and said absorbent core to vary.

12. The absorbent article of claim 11 wherein said backsheet is elastically extensible in an area between said absorbent core and said cushioning member to allow spacing between said cushioning member and said absorbent core to vary.

13. The absorbent article of claim 1 wherein said back waist region comprises an elastically extensible non-woven material.

14. The absorbent article according to claim 1, said absorbent core further having a transverse center line located midway between said front transverse edge and said back transverse edge, a front half section located between said transverse centerline and said front transverse edge, and a back half section located between said transverse centerline and said back transverse edge,
   wherein the average basis capacity of said back half section is greater than the average basis capacity of said front half section.

15. The absorbent article of claim 14, wherein the ratio of said average basis capacity of said back half section and said average basis capacity of said front half section is between about 1.1 and 3.

16. The absorbent article of claim 14, said absorbent core further having absorbent gelling material in said front half section and said back half section, wherein the weight of said absorbent gelling material in said back half section is greater than the weight of said absorbent gelling material in said front half section.

17. The absorbent article of claim 16, wherein between about 55% and 100% by weight of said absorbent gelling material is in said back half section.

18. The absorbent article of claim 16, wherein between about 65% and 80% by weight of said absorbent gelling material is in said back half section.

19. The absorbent article of claim 1, said backsheet back waist region comprising a portion extending beyond said back transverse edge of said absorbent core and having a z-like inward fold forming a liquid barrier, said inward fold having an inward part and an outward part, said inward part and said outward part being mutually connected along a fold line located in proximity to said back transverse edge, wherein said fold line is attached to said topsheet and said outward section is attached to said inward section.

20. The absorbent article of claim 1 further comprising a stand-up barrier cuff having a proximal edge which is joined to said absorbent article and a distal edge comprising an elastic element for spacing said distal edge away from said topsheet.

21. The absorbent article of claim 20 wherein said proximal edge is located between said back transverse edge of said absorbent core and said back waist edge of said backsheet.

* * * * *